US012667301B2

(12) United States Patent
Fan et al.

(10) Patent No.: US 12,667,301 B2
(45) Date of Patent: Jun. 30, 2026

(54) TRANSEPIDERMAL WATER LOSS MEASUREMENT DEVICE

(71) Applicant: THE REGENTS OF THE UNIVERSITY OF MICHIGAN, Ann Arbor, MI (US)

(72) Inventors: Xudong Fan, Saline, MI (US); Anjali Devi Sivakumar, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 252 days.

(21) Appl. No.: 18/428,514

(22) Filed: Jan. 31, 2024

(65) Prior Publication Data

US 2024/0252099 A1 Aug. 1, 2024

Related U.S. Application Data

(60) Provisional application No. 63/442,631, filed on Feb. 1, 2023.

(51) Int. Cl.
| | |
|---|---|
| *A61B 5/00* | (2006.01) |
| *B01D 53/02* | (2006.01) |
| *B01D 53/26* | (2006.01) |

(52) U.S. Cl.
CPC ............ *A61B 5/4266* (2013.01); *A61B 5/681* (2013.01); *B01D 53/02* (2013.01); *B01D 53/266* (2013.01);
(Continued)

(58) Field of Classification Search
CPC ... A61B 5/4266; A61B 5/4875; A61B 5/4878; A61B 5/14517; A61B 2562/4875;
(Continued)

(56) References Cited

U.S. PATENT DOCUMENTS 3,139,085 A * 6/1964 Custance ............. A61B 5/4261
236/44 R
3,318,302 A * 5/1967 Adams ................. A61B 5/4266
600/307
(Continued)

FOREIGN PATENT DOCUMENTS

| JP | 2003135406 A * | 5/2003 |
|---|---|---|
| JP | 2017006554 A | 1/2017 |

(Continued)

OTHER PUBLICATIONS

JP 2021-83931 A English Translation (Year: 2021).*
(Continued)

*Primary Examiner* — Adam J Eiseman
(74) *Attorney, Agent, or Firm* — Harness, Dickey & Pierce, P.L.C.

(57) ABSTRACT

Transepidermal water loss (TEWL) measurement approach is presented that achieves accurate and continuous monitoring completely independent of ambient environmental variations. This new measurement approach uses short dry air purges to dry the skin surface and the water vapor collection chamber, thus refreshing the measurement site each time during skin barrier analysis. These dry air purges help maintain a highly controlled localized measuring environment without disturbing any inherent skin properties, enabling one to produce reproducible TEWL results. A mathematical model developed based on Fick's laws of diffusion is presented, and shown to have excellent agreement with the mathematical model of a commercial TEWL device. The application of this mathematical model in deciphering the TEWL values from the transient microclimate behavior in the vapor measuring chamber of the new TEWL approach is also discussed.

14 Claims, 11 Drawing Sheets

(52) U.S. Cl.
CPC . *A61B 2560/0252* (2013.01); *A61B 2562/029* (2013.01); *B01D 2257/702* (2013.01); *B01D 2257/80* (2013.01)

(58) Field of Classification Search
CPC .... A61B 10/0064; G01N 25/56; G01N 25/58; G01N 25/60; G01N 25/66; G01N 25/68
See application file for complete search history.

(56) References Cited

U.S. PATENT DOCUMENTS

| | | | | |
|---|---|---|---|---|
| 4,050,995 | A * | 9/1977 | Bredeweg | G01N 27/423 |
| | | | | 204/430 |
| 4,461,303 | A * | 7/1984 | Refojo | A61B 3/101 |
| | | | | 600/307 |
| 5,131,390 | A * | 7/1992 | Sakaguchi | A61B 5/4261 |
| | | | | 600/573 |
| 6,287,255 | B1 * | 9/2001 | Endo | A61B 3/101 |
| | | | | 600/584 |
| 6,439,028 | B1 | 8/2002 | Imhof | |
| 6,533,725 | B1 * | 3/2003 | Endo | A61B 5/4266 |
| | | | | 600/307 |
| 6,966,877 | B2 | 11/2005 | Lahtinen | |
| 7,247,137 | B2 * | 7/2007 | Tsuda | A61B 5/00 |
| | | | | 600/300 |
| 7,884,446 | B2 | 2/2011 | Mazur et al. | |
| 8,143,686 | B2 | 3/2012 | Mazur et al. | |
| 8,697,935 | B2 | 4/2014 | Daanen | |
| 8,802,549 | B2 | 8/2014 | Sickler et al. | |
| 8,860,034 | B2 | 10/2014 | Prushinskiy et al. | |
| 9,271,676 | B2 | 3/2016 | Alanen et al. | |
| 9,907,506 | B2 * | 3/2018 | Mihara | A61B 5/443 |
| 10,431,455 | B2 | 10/2019 | Abere et al. | |
| 2006/0079062 | A1 | 4/2006 | Mazur et al. | |
| 2007/0263974 | A1 | 11/2007 | Khrushchev et al. | |
| 2008/0032237 | A1 | 2/2008 | Wong et al. | |
| 2008/0125631 | A1 | 5/2008 | Imhof | |
| 2010/0219506 | A1 | 9/2010 | Gupta et al. | |
| 2011/0121206 | A1 | 5/2011 | Mazur et al. | |
| 2019/0167184 | A1 | 6/2019 | Han et al. | |

FOREIGN PATENT DOCUMENTS

| | | | | | |
|---|---|---|---|---|---|
| JP | 2019088368 | A | * | 6/2019 | |
| JP | 2020146372 | A | * | 9/2020 | |
| JP | 2021083931 | A | * | 6/2021 | |
| JP | 2024120367 | A | * | 9/2024 | |
| KR | 20120107349 | A | | 10/2012 | |
| KR | 20150135142 | A | | 12/2015 | |
| KR | 20190088246 | A | | 7/2019 | |
| KR | 20200057533 | A | | 5/2020 | |
| WO | WO-2019143082 | A1 | * | 7/2019 | A61B 5/00 |
| WO | WO-2022243872 | A1 | | 11/2022 | |

OTHER PUBLICATIONS

JP 2019-088368 A English Translation (Year: 2019).*
Klotz, Tanja et al., "Devices measuring transepidermal water loss: A Systematic review of measurement properties" Skin Res Technol. Apr. 12, 2022;28:497-539.
International Search Report and Written Opinion of the ISA issued in PCT/US2024/013977, mailed Jun. 3, 2024; ISA/US.

* cited by examiner

① Read RH and Temperature from the RH and Temperature Sensors

② Calculate Water Vapor Concentration $C_3$ at the RH-T Sensor Location

③ Calculate Water Vapor Concentration at Two Points ($C_1$ and $C_2$) Near the Skin Surface ④ Calculate Water Vapor Flux (J) Near the Skin Surface Step #1

TRANSEPIDERMAL WATER LOSS MEASUREMENT DEVICE

CROSS-REFERENCE TO RELATED APPLICATIONS

This application claims the benefit of U.S. Provisional Application No. 63/442,631, filed on Feb. 1, 2023. The entire disclosure of the above application is incorporated herein by reference.

GOVERNMENT CLAUSE

This invention was made with government support under TR004066 awarded by the National Institutes of Health. The government has certain rights in the invention.

FIELD

The present disclosure relates to a water loss measurement device.

BACKGROUND

Recent advancements in skin barrier research have brought to light the intricate mechanisms underlying various common skin diseases. This significant progress has been made following the discovery of the filaggrin mutation (FLG) in patients with atopic dermatitis (AD). FLG, a critical epidermal protein essential for skin barrier formation, represents a major risk factor for AD. Moreover, investigations have revealed a correlation between the FLG mutation and conditions such as asthma and food allergies, even in the absence of AD. Additionally, a recent study has highlighted the significant potential of skin barrier integrity as a valuable biomarker for the early detection of life-threatening food anaphylaxis, enabling timely intervention before symptom onset.

Apart from the impaired skin barrier associated with common atopic skin disease conditions, climatic conditions, particularly during winter, can further exacerbate skin barrier dysfunction due to decreased levels of lignoceric and heptadecanoic acids. Additionally, chronic exposure to air pollution plays an important role in disrupting the skin barrier. Air pollution and particulate matter have the potential to cause substantial damage to the protective epithelial barrier by inducing oxidative stress through reactive oxygen species. This oxidative barrier disruption, in turn, can aggravate dermatologic conditions like AD and trigger immune system activation cascades. Hence, early identification of skin barrier dysfunction in individuals affected by these factors is essential for timely preventive care interventions.

Different skin analysis methods, like transepidermal water loss (TEWL) measurement, which is also known as insensible sweating rate measurement, Raman spectroscopy, and imaging techniques such as optical coherence tomography and laser scanning microscopy, have been developed over the years to monitor skin barrier integrity. Owing to its non-invasive and cost-effective nature, TEWL is most widely used as a parameter for evaluating skin barrier function compared to the other skin barrier analysis methods. It is known that the entire body can produce both sensible sweat (through sweat glands due to external stimuli such as heat) and insensible sweat without any external stimulus. Insensible sweating results from water within the body osmotically diffusing and unconsciously evaporating from the inner dermis and epidermis to the outermost layer of the skin called stratum corneum (SC), driven by a water gradient. Most insensible sweat evaporates from the skin surface into the surrounding environment, which is TEWL, while a portion is retained within the stratum corneum to maintain skin hydration. In healthy skin, efficient moisture retention leads to normal TEWL values (~5-40 $g/m^2hr$, depending on body locations and ages), whereas high or low TEWL values indicate skin barrier dysfunction or intact/recovered skin barrier, respectively.

Over the past two decades, various commercial hygrometer-based TEWL measurement devices have been developed for clinical and cosmetic applications, including, for example, Tewameter device, GPSKIN device, Vapometer device, AquaFlux device, and DermaLab device. All these commercial devices are configured in an open or closed chamber format to estimate the TEWL values by analyzing the microclimate created by the diffusive water vapor flux from the skin. The open chamber TEWL devices are susceptible to environmental factors, such as ambient temperature and humidity, and air flow. Consequently, the examinees are required to wait in the test environment, where temperature and humidity (and possibly air flow) are controlled for a certain period of time (~20 min) before measurement. No motion is allowed during the measurement. On the other hand, the closed chamber TEWL devices may encounter a problem of water accumulation inside the chamber. Furthermore, the initial water content on the skin surface and initial humidity inside the chamber may affect the TEWL measurement for some of closed chamber TEWL devices. Finally, nearly all commercial TEWL devices are bulky and cannot be made wearable.

This section provides background information related to the present disclosure which is not necessarily prior art.

SUMMARY

This section provides a general summary of the disclosure, and is not a comprehensive disclosure of its full scope or all of its features.

In one aspect, a transepidermal water loss measurement device is presented. The measurement device is comprised of: a housing having a measurement chamber enclosed therein, where the measurement chamber has an opening configured to be placed against skin of a subject. An inlet duct resides the housing and provides a fluidic channel into the measurement chamber, and an outlet duct resides in the housing and provides a fluidic channel into the measurement chamber. A relative humidity sensor is arranged adjacent to or in the measurement chamber and configured to measure relative humidity in the measurement chamber; whereas, a temperature sensor is also arranged adjacent to or in the measurement chamber and configured to measure temperature in the measurement chamber.

In one embodiment, a pump is fluidly coupled to the inlet duct and operates to move air through the measurement chamber. A controller operably couples to the pump and is in data communication with the humidity sensor and the temperature sensor.

During a drying phase, the pump is turned on and, during a measurement phase, the pump is turned off. From the measured relative humidity and the measured temperature, the controller determines water loss thru the skin adjacent to the opening of the measurement chamber.

In another aspect, a method is presented for measuring water loss through skin of a subject. The method includes: forming a measurement chamber, where the measurement chamber has an opening configured to be placed against the skin of the subject; reducing humidity in the measurement chamber during a drying phase; measuring relative humidity in the measurement chamber over time during a measurement phase that immediately follows the drying phase; measuring temperature in the measurement chamber during the measurement phase; and calculating water loss through the skin based on the measured relative humidity and the measured temperature.

Reducing humidity in the measurement chamber may include one or more of circulating air through the measurement chamber during the drying phase, filtering moisture from the air circulating through the measurement chamber, and filtering hydrocarbons from the air circulating through the measurement chamber.

The method may further include calculating water loss through the skin before the drying phase, calculating water loss through the skin after the drying phase, and calculating an indicator of skin rehydration based on the calculated water loss before and after the drying phase.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

4

Figure 1A:
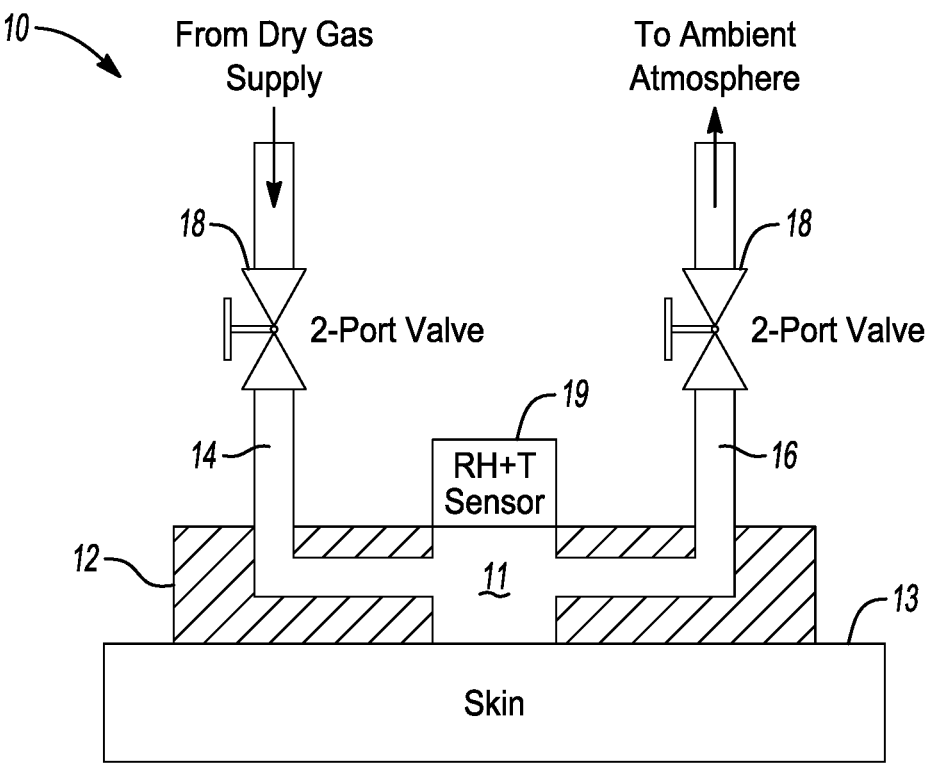
FIG. 1A is a schematic for a proposed transepidermal water loss (TEWL) measurement device in accordance with a first embodiment.

Corresponding reference numerals indicate corresponding parts throughout the several views of the drawings.

DETAILED DESCRIPTION

Example embodiments will now be described more fully with reference to the accompanying drawings.

Figure 1B:
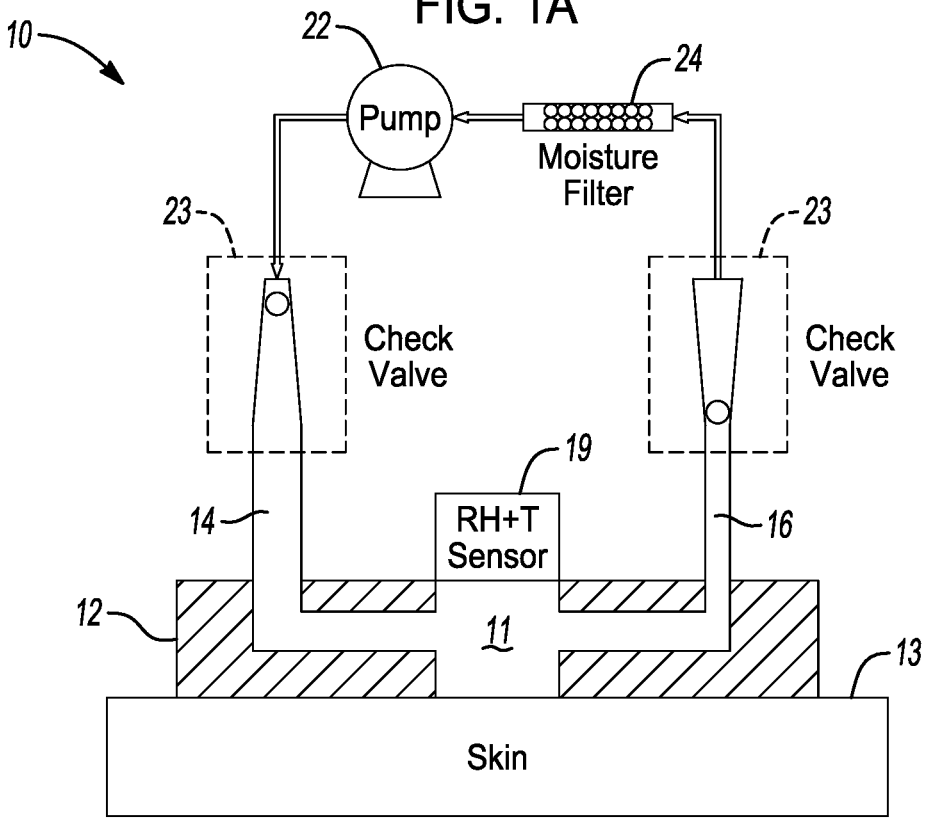
FIG. 1B is a schematic for the proposed transepidermal water loss (TEWL) measurement device in accordance with a second embodiment.

FIGS. 1A and 1B depict a proposed transepidermal water loss (TEWL) measurement device 10. The measurement device 10 is comprised of a housing 12 having a measurement chamber 11 enclosed therein. The measurement chamber has an opening configured to be placed against skin 13 of a subject. The housing further includes an inlet duct 14 and an outlet duct 16. The inlet duct 14 provides a fluidic channel to the measurement chamber, where one end of the fluidic channel is accessible outside of the housing and other end of the fluidic channel connects into the measurement chamber. Likewise, the outlet duct 16 provides a fluidic channel to the measurement chamber, where one end of the fluidic channel is accessible outside of the housing and other end of the fluidic channel is connected into the measurement chamber. Different arrangements for the inlet and outlet ducts are contemplated by this disclosure.

The inlet duct 14 and the outlet duct 16 enable air to be moved through the measurement chamber in order to flush out any accumulated water vapor from the chamber and remove residual water on the skin surface before each measurement. In one embodiment, the air can be provided by an external source, such as a clean air cylinder as seen in FIG. 1A. Two port valves 18 can be placed into each fluidic outlet or channel. During a drying phase, the two port valves 18 are in an open position to thereby allow the air to move through the measurement chamber 11; whereas, during a measurement phase, the two port valves 18 are in a closed position to thereby seal the measurement chamber 11.

In another embodiment, a pump 22 can be used to circulate air in a closed system through the measurement chamber 11 as seen in FIG. 1B. That is, the air inside the measurement chamber is circulated via the pump through the system In lieu of the two port valves, check valves 23 may be used to regulate the flow of the air through the system. In this embodiment, it is advisable the air be conditioned before moving through the measurement chamber 11. To do so, the air may be passed through one or more filters 24. For example, a filter may be configured to remove moisture from the air moved by the pump into the measurement chamber. An example filter is the moisture humidity filter commercially available from Forensics Detectors. In another example, a filter may be configured to remove hydrocarbons from the air moved by the pump into the measurement chamber. An example filter is the molecular sieve gas filter commercially available from Forensics Detectors. In some embodiments, both types of filters are implemented. This arrangement is particularly suitable for a wearable device (e.g., similar to a watch). Other types of filters also fall within the scope of this disclosure. It is envisioned that in other embodiments air from outside the system may be drawn in and circulated through the system. In lieu of a pump, it is also envisioned that the system may be moved through the measurement chamber by creating a vacuum.

In some embodiments, the measurement device 10 includes means for controlling temperature in the measurement chamber and/or at the skin surface. Typically, there is a desire to cool the measurement chamber and/or at the skin surface. Cooler air (temperature below 24 degrees C.) may be used to suppress thermal (sensible) sweating so that transepidermal water loss (i.e., insensible sweating) can be measured more accurately. Cooling techniques may include but are not limited to cooling gels applied to the skin (e.g., cooling sheets from Be Koool) and a thermoelectric cooler disposed in the measurement chamber (e.g., micro modules commercially available from TE Technology, Inc.). In some instance, it may be desired to heat the measurement chamber using a heater disposed in the measurement chamber.

The measurement device 10 further includes a relative humidity sensor and a temperature sensor arranged adjacent to or in the measurement chamber 11. The relative humidity sensor is configured to measure relative humidity in the measurement chamber; whereas, the temperature sensor is configured to measure temperature in the measurement chamber. The two sensors may be integrated into a single device or implemented as two separate devices. It is also envisioned that other types of sensors can be placed in the chamber including but not limited to pressure sensor and galvanic skin response sensor to measure the elasticity and conductance, respectively, of the skin.

In the example embodiment, a single integrated sensing device 19 is placed on top of the housing with a sensing surface facing inward and exposed to the interior of the measurement chamber 11 (also referred to herein as RH+T sensor). The relative humidity and temperature transients inside the measurement chamber due to the diffused water flux from the skin are monitored with integrated sensing device (for instance, 2.5 mm from the skin surface). In other embodiments, the integrated sensing device (or two separate sensors) may be placed inside the measurement chamber 11, for example along a side wall or on the ceiling of the measurement chamber.

Water loss through the skin can then be determined by a controller 20 from these sensor readings using Fick's first and second laws of diffusion. To do so, the controller 20 is in data communication with the relative humidity sensor and/or the temperature sensor. The mathematical modeling of the measurement chamber is explained in more detail below. The controller 20 is also operably coupled to the pump 22. In an exemplary embodiment, the controller 20 is implemented as a microcontroller. It should be understood that the logic for the control of the measurement device 10 can be implemented in hardware logic, software logic, or a combination of hardware and software logic. In this regard, controller 20 can be or can include any of a digital signal processor (DSP), microprocessor, microcontroller, or other programmable device which are programmed with software implementing the above described methods. It should be understood that alternatively the controller is or includes other logic devices, such as a Field Programmable Gate Array (FPGA), a complex programmable logic device (CPLD), or application specific integrated circuit (ASIC). When it is stated that controller 20 performs a function or is configured to perform a function, it should be understood that controller 20 is configured to do so with appropriate logic (such as in software, logic devices, or a combination thereof).

It should be pointed out that the proposed measurement device has all the benefits of a closed chamber system: no ambient interferences such as airflow or convection, humidity, and temperature changes. In addition, no water accumulates inside of the chamber. Therefore, it can be employed for continuous monitoring of water loss for long periods of time. In addition, it consumes much less power than the condenser-based approach and causes no discomfort to the subjects under test.

Figure 2:
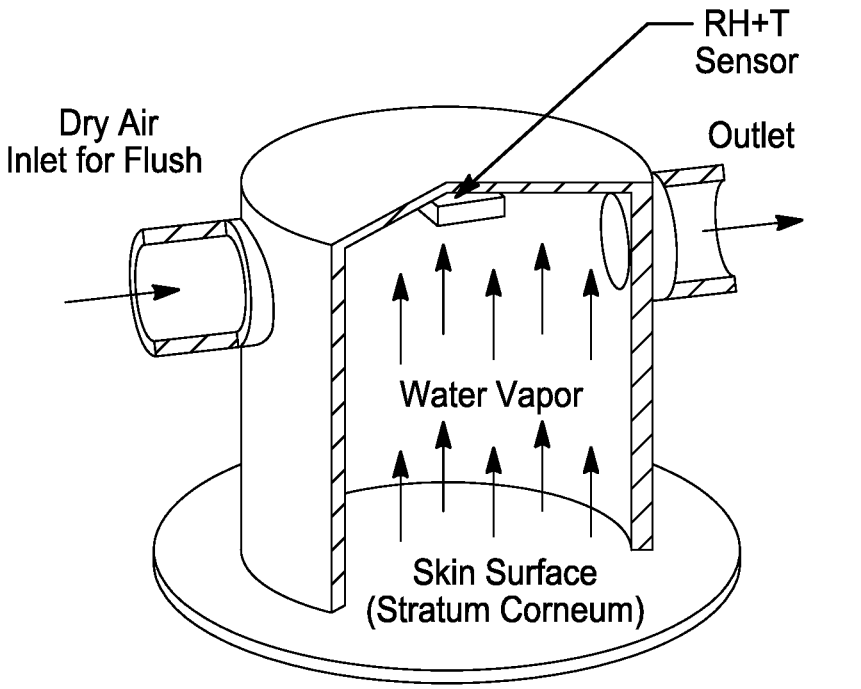
FIG. 2 is a cross-section view of the TEWL measurement device.
Figure 3:
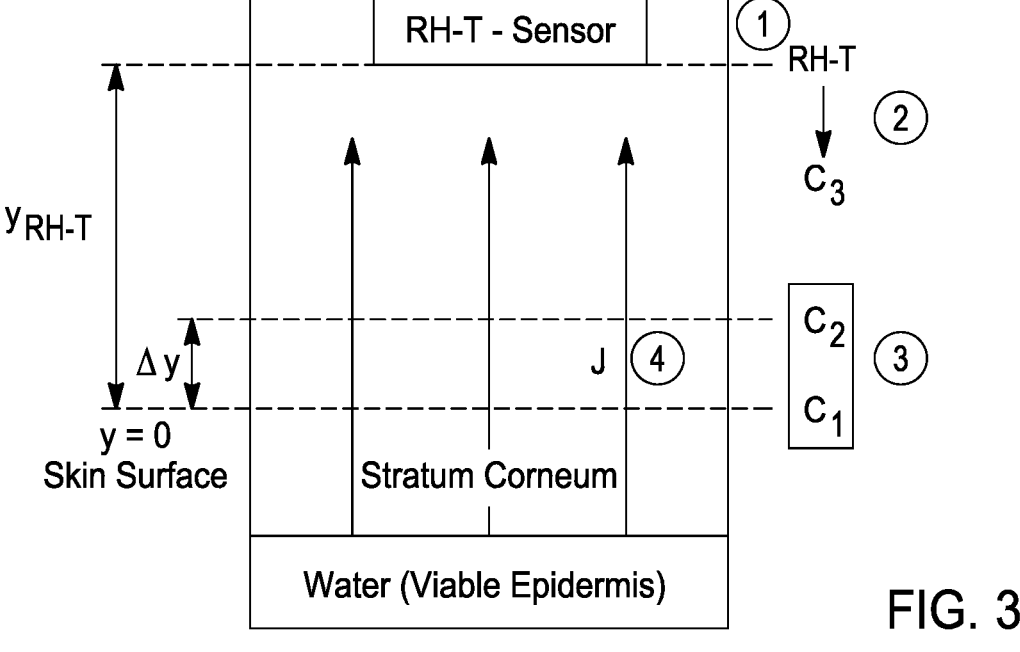
FIG. 3 is a schematic of the TEWL measurement device and the related model and parameters.

Unlike the open-chamber and condenser-based approach, the water vapor concentration and hence the concentration gradient and evaporative water vapor flux in the chamber change over time because of water vapor accumulation during the water vapor flux measurement period. With reference to FIGS. 2 and 3, this process can be modeled using 1-dimensional Fick's second law of diffusion, i.e., $$\frac{\partial C}{\partial t} = D \frac{\partial^2 C}{\partial y^2}, \tag{1}$$

where C is the concentration of water vapor at any point, y, along the chamber height at time t. D is the diffusion coefficient of water vapor in the air inside the chamber. Here, assume that there is no convection inside the chamber and the water vapor motion is caused only by diffusion. In the model, the following boundary and initial conditions are used:

1. $C (y>0, t=0)=C_0$. $C_0$=Initial concentration of water vapor in the chamber.
2. $C (y=0, t>0)=C_s$. Here, assume that the water source (the skin) is a non-depleting source that provides constant water vapor concentration $C_s$ on the skin surface.
3. $C (y=\infty, t=0)=0$. Here, assume that the length of the chamber is infinite, although a closed chamber with a finite height (or volume) was used in our actual device. This assumption significantly simplifies the mathematical modeling, as the concentration at any spatial point at a given time can be analytically calculated (see Eq. (2) below).

Solving Eq. (1) using the above boundary and initial conditions yields $$C(y, t) = (C_s - C_0) erfc \left( \frac{y}{2\sqrt{Dt}} \right) + C_0. \tag{2}$$

Equation (2) can thus be used to calculate the concentration transient of water vapor at any spatial point along the chamber height in the chamber, if the water vapor concentration at any other spatial point at a given time is known. Therefore, using Equation (3), the water vapor concentration at skin surface ($C_s$) can be calculated from $C_3$ obtained by the RH-T sensor (placed at a distance of $y_{RH-T}$ from the skin surface). This $C_s$ value can later be used to calculate the water vapor concentration at two spatial points very close to the skin surface (i.e., $C_1$ and $C_2$ in FIG. 3) using Eq. (2).

$$C_s = \frac{(C_3 - C_0)}{erfc \left( \frac{y_{RH-T}}{2\sqrt{Dt}} \right)} + C_0. \tag{3}$$

Finally, Fick's first law (Eq. (4)) is used to calculate the water vapor flux from the calculated water vapor concentrations at two spatial points near the skin, i.e., $$\text{Water vapor flux} = -J = D \frac{C_1 - C_2}{\Delta y} \tag{4}$$

Figure 4:
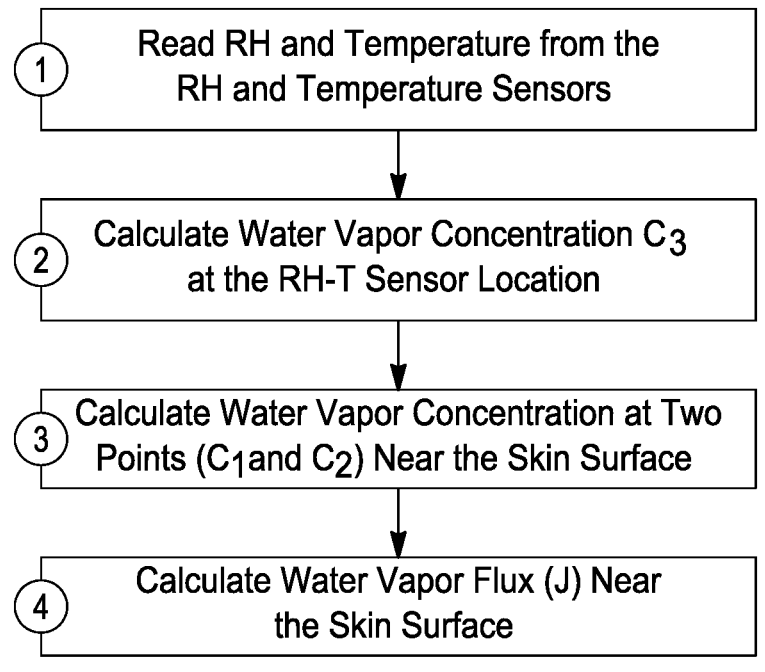
FIG. 4 is a flowchart showing the water vapor flux calculation using the TEWL measurement device.

The overall process is illustrated in FIG. 4.

Practically, $C_0$, the initial water vapor concentration inside the chamber, is obtained by the RH sensor right before the measurement starts. It consistently decreases down to ~5% after purge. The spatial point for $C_1$ is chosen to be y=0, i.e., the skin surface. It should be noted that in the above model, one can assume that the humidity sensor response is instantaneous. Practically, the humidity sensor has a finite response time.

Figure 5:
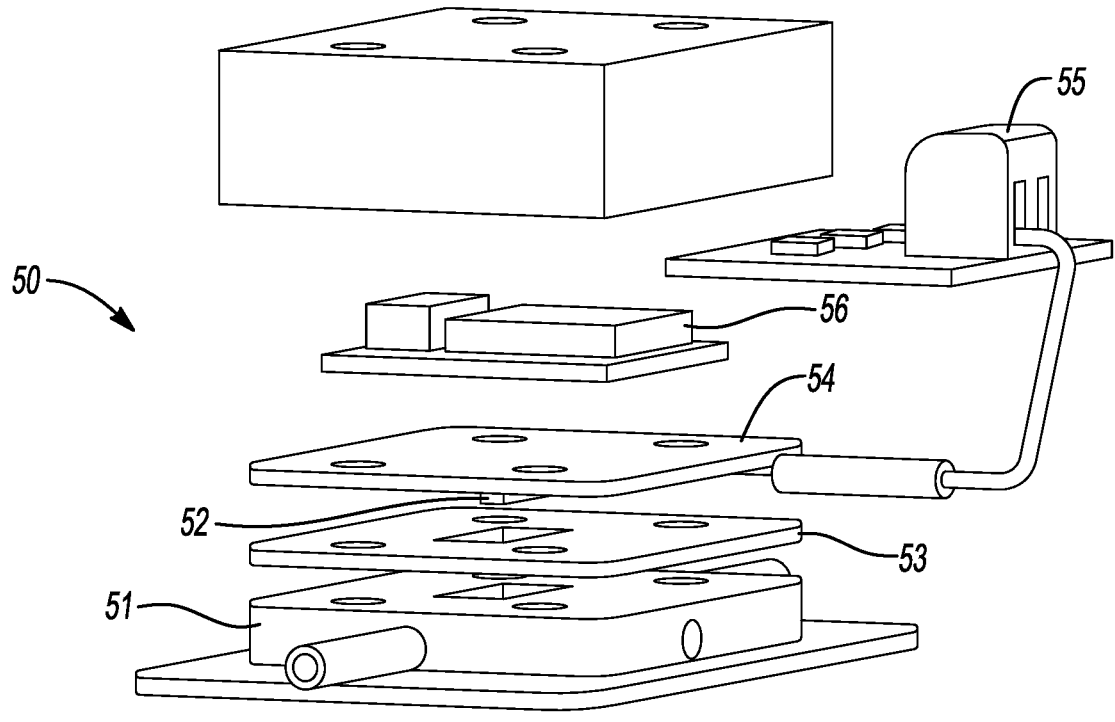
FIG. 5 is an exploded view on an example implementation for the TEWL measurement device.

To characterize the proposed measurement device 10, a TEWL module 50 was constructed that had a 3D-printed chamber 51 with dimensions of 4.5 mm (width)×8 mm (length)×4.75 mm (height) using High-Temperature Resin (P/N: RS-F2-HTAM-02, Formlabs) as seen in FIG. 5. A capacitive polymer-based RH sensor 52 (e.g., SHTC3, Sensirion) and the corresponding breakout board (Adafruit) were used to monitor the RH transients. The RH sensor 52 was placed on top of the chamber ceiling. The bare electronics exposed on the sensor board 54 were protected with a waterproof plastic wrap. Further, to ensure a tight seal between the board 54 and the chamber 51, a flexible 3D-printed gasket 53 using Flexible 80A resin (P/N: RS-F2-FL80-01, Formlabs) was sandwiched between the sensor board 54 and the chamber 51. Since the integrated temperature sensor in SHTC3 was observed to provide inaccurate temperature readings in the presence of a non-uniform heat source, for instance, skin, an external K-Type thermocouple (P/N: 270, Adafruit) was installed near the SHTC3 to measure temperature transients more accurately inside the chamber (near the RH sensor). The thermocouple 55 was capped with a single layer of Kapton tape (substrate thickness—0.025 mm and adhesive thickness—0.05 mm; P/N: EL-CP-022, Elegoo) to protect the thermocouple from moisture accumulated in the chamber. The addition of Kapton tape on the thermocouple was shown to have no impact on the thermocouple's final temperature reading. The temperature was recorded with a breakout board with a microcontroller 56 MCP9600 (P/N: 4101, Adafruit). The RH and temperature transient data from the sensors was streamed to a laptop in real time with Seeed Studio nRF52840 Sense (Microcontroller Unit) using LabVIEW. Further, the time-controlled dry air or N2 flushes were provided to the chamber from an external tank with the help of two electromechanical valves (P/N: LFVA1220210H, LEE Company).

Figure 6:
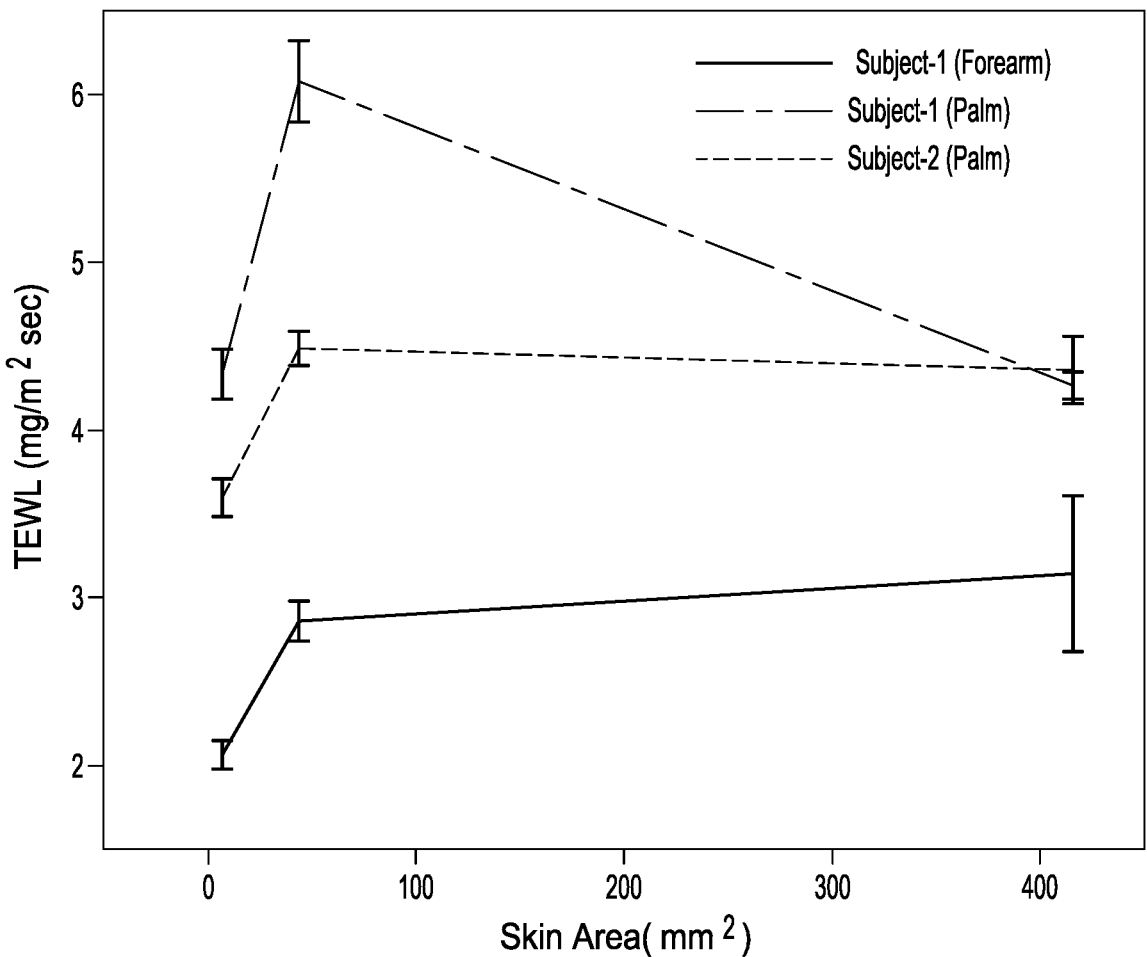
FIG. 6 is a graph showing water loss values recorded for two subjects at two different locations with different exposed skin areas.

Evaporative flux (or) TEWL is a quantity independent of the surface area. It can be observed from FIG. 6 that TEWL values measured by the measurement device 10 are indeed independent of the skin area under measurement. Due to the differences in skin morphology across the body, studies have shown that the TEWL values recorded at the palm are higher than the TEWL values at the forearm. The proposed measurement device 10 also records this trend when tested at these two locations as portrayed in FIG. 6.

Figure 7:
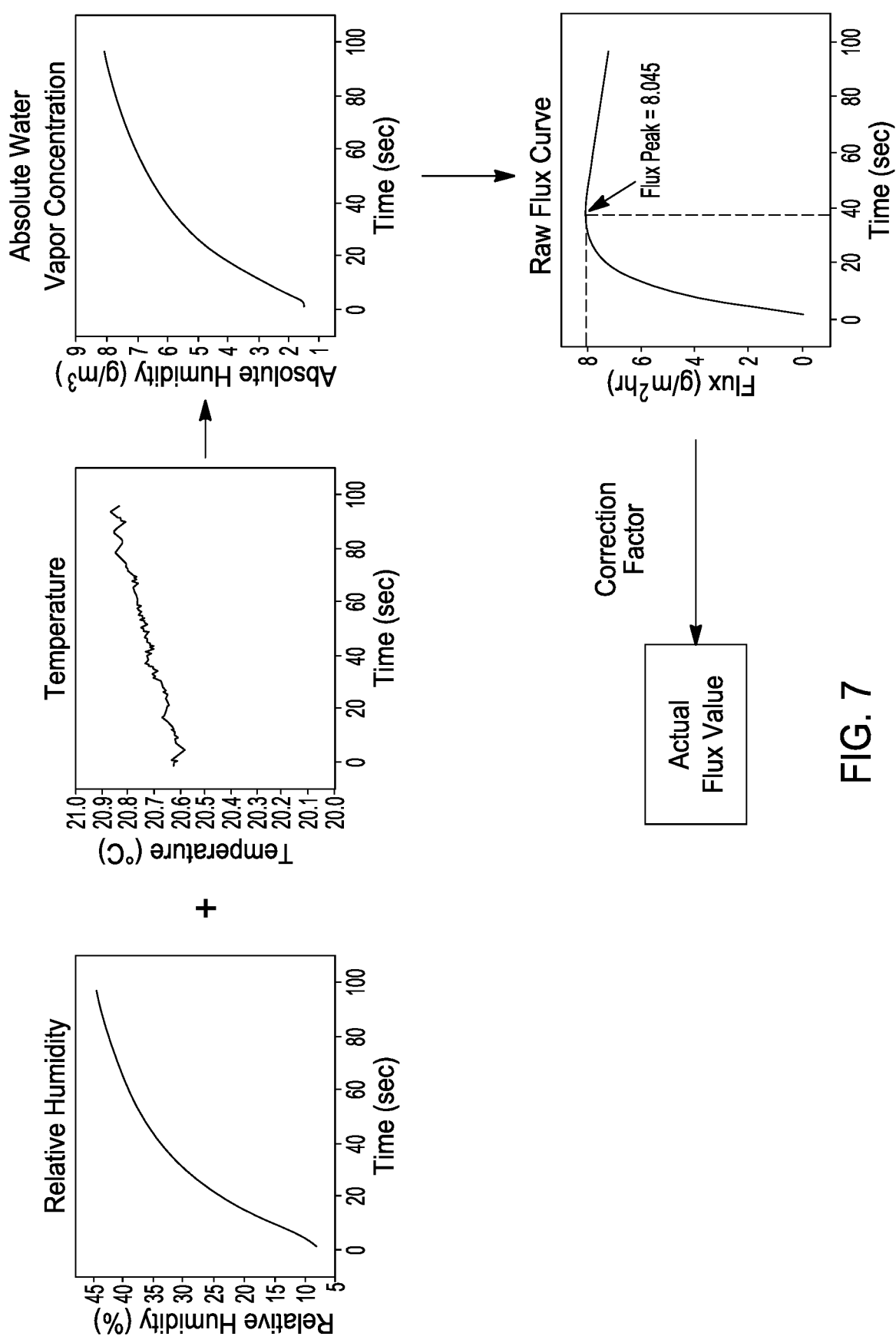
FIG. 7 illustrates a process flow to obtain actual water vapor flux value using the TEWL measurement device.

FIG. 7 illustrates a process flow to obtain actual water vapor flux value using the TEWL measurement device 10. First, the RH-T temporal readings are used to calculate the corresponding absolute water vapor concentration (or absolute humidity). Second, the temporal water vapor flux curve is calculated using the mathematical model described above. Third, the maximal water vapor flux and the corresponding time were recorded. Finally, a correction factor was used to account for any non-idealities (such as nonlinear time constant of the RH sensor).

Figure 8:
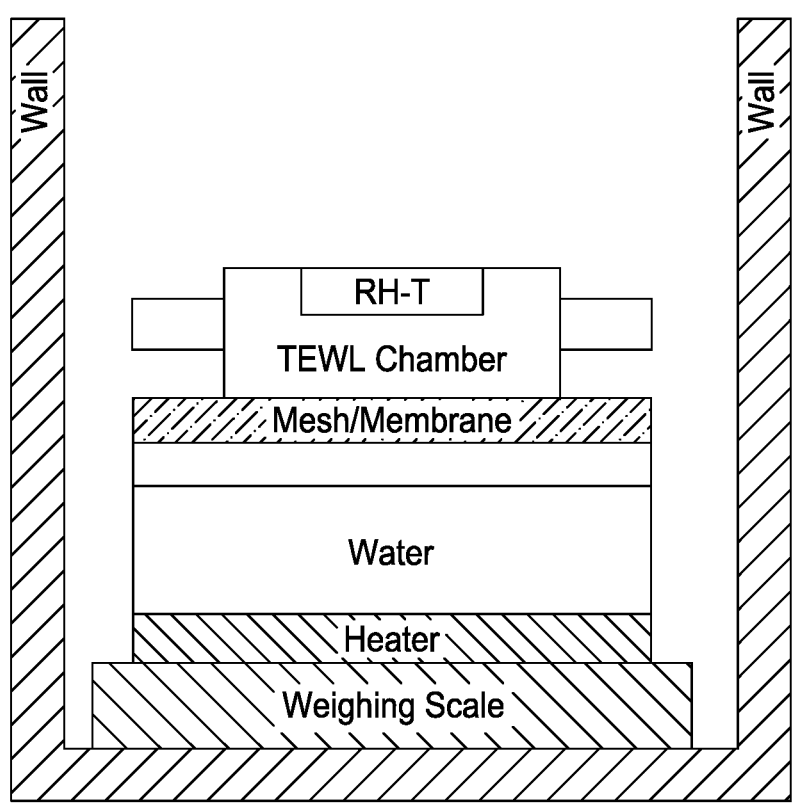
FIG. 8 is a schematic of a wet-cup setup to generate different water vapor flux values.

With reference to FIG. 8A, a standard wet-cup method with artificial skin was used to generate known flux values and obtain the correction factor. To ensure precise measurements across a wide flux range, two distinct wet cup setups were used: wet cup setup-1 (WCS1) and wet-cup setup-2 (WCS2). In WCS1, a polystyrene petri dish (diameter: 54.4 mm) filled with water at room temperature (~19° C.) was employed and the water evaporation rate (i.e., water vapor flux) was controlled by using two different types of semipermeable membranes, one with fine pores (OpSite Flexigrid, Smith and Nephew, England) and one with coarse pores (304 Stainless Steel 150 Mesh, Uxcell). WCS2 employed a wireless mug with integrated heater (Vsitoo, Amazon) filled with water and covered by a semipermeable membrane (304 Stainless Steel 150 Mesh, Uxcell). Water temperature was controlled to generate different evaporation rates. During the water vapor flux measurements with the WCS-2, the initial 20 mins of wait time was allotted after TEWL module is placed on the wet-cup setup to allow the chamber to reach thermal equilibrium with the wet-cup before start of water vapor flux measurement.

A weighing scale was used in both these setups to continuously measure the loss of water mass at intervals of approximately three seconds over a duration of at least 10 minutes. WCS1 employed a high-resolution weighing scale (P/N: USS-DBS83-120G, U.S. Solids) to accurately measure small water loss weights; whereas, WCS2 used a larger range weighing scale (P/N: JFDBS00058-500G, U.S. Solids). The periphery of the weighing scale and water cup was surrounded by a plastic rigid wall to avoid any measurement errors due to the convection of the ambient air. The water vapor flux values were obtained by dividing the water mass loss by both time and the area of the petri dish or mug. As a result of this comprehensive process, the wet-cup setups could generate seven flux data points ranging from 8 g/m² hr to 300 g/m² hr.

To meet the needs of dynamic RH measurement in TEWL device 10, it is crucial to employ an RH sensor with an instantaneous response, i.e., zero delay. But in practice, these sensors have a finite delay that affects the accuracy of the flux measurements. In an example embodiment, the RH sensor (i.e., SHTC3) used in the TEWL device is a simple capacitive sensor with a moisture-sensitive layer that operates on Fick's law of diffusion. Its response time may be affected by the characteristics of the sensor such as plate structure, thickness of the moisture-sensitive layer, ambient temperature, and humidity, etc. For example, when humid air comes into contact with a colder sensor surface, moisture condensation may occur, which may impact the RH sensor's response time. The condensation becomes more severe during measurements at higher RH levels and is one of the primary causes for the nonlinear response time of the RH sensor.

Figure 9:
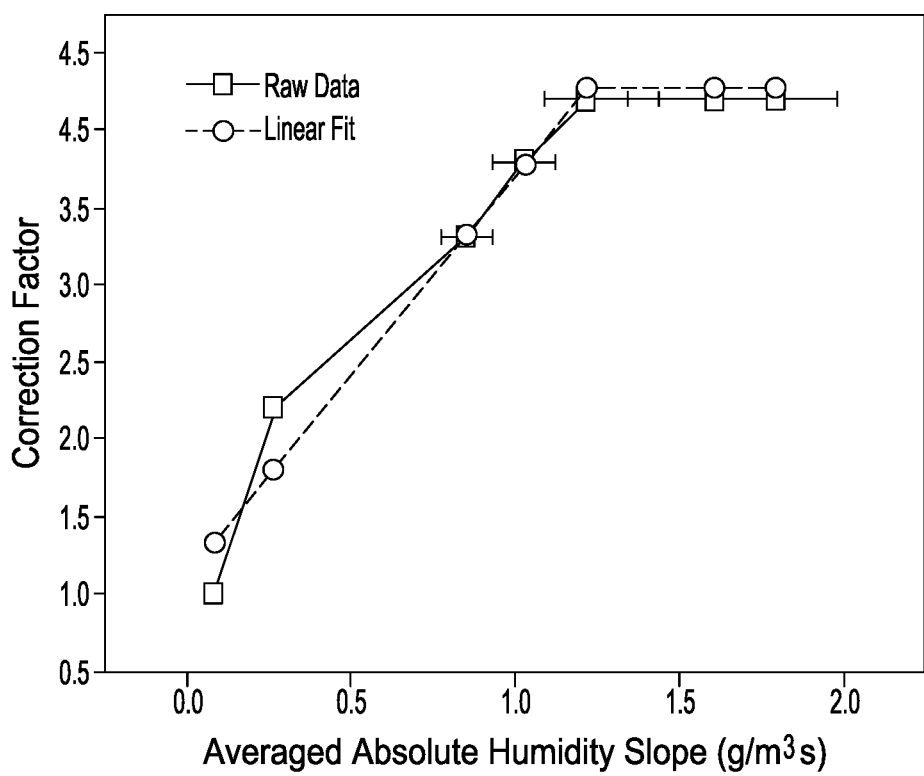
FIG. 9 is a graph showing a correction factor vs. averaged absolute water vapor concentration (or humidity) slope measured by the TEWL device, where the red curve is the linear fit up to 1.2 g/m³s and error bars are obtained from at least ten measurements.

An algorithm was developed to accommodate the aforementioned non-idealities in actual water vapor flux measurements. In this algorithm, a correction factor is obtained by dividing the true water vapor flux measured with the wet-cup experiment shown in FIG. 8 by the maximal flux value in the raw flux curve obtained by the TEWL device 10 according to the procedures illustrated in FIG. 7. FIG. 9 shows that the correction factor depends linearly on the absolute humidity slope (i.e., the water vapor concentration vs. time) averaged at 2 s, 4 s, and 6 s before the flux apex time (see FIG. 7 for illustration of a flux peak). This can be understood as follows. At a low water vapor flux, the flux curve obtained by the TEWL device 10 rises very slowly. Therefore, the slow RH sensor response does not affect the flux measurement. Consequently, the correction factor is close to unity. At an increased water vapor flux, the flux curve obtained from the TEWL device 10 rises more rapidly. Consequently, the slow RH sensor response has increased impact on the flux measurement. Therefore, the correction factor becomes larger.

It should be noted that the correction factor curve exhibits linearity for the averaged absolute humidity slope below 1.2 $g/m^3s$ (corresponding to a true water vapor flux value of 200 $g/m^2$ hr), beyond which it levels off. This saturation phenomenon is indicative of reaching the upper limit of water vapor capacity that the designed chamber can hold within the measurement time (~60 s) and the occurrence of water condensation. Depending on the application's dynamic range, the chamber's height can be increased, thereby augmenting its volume and capacity for water vapor.

Figure 10:
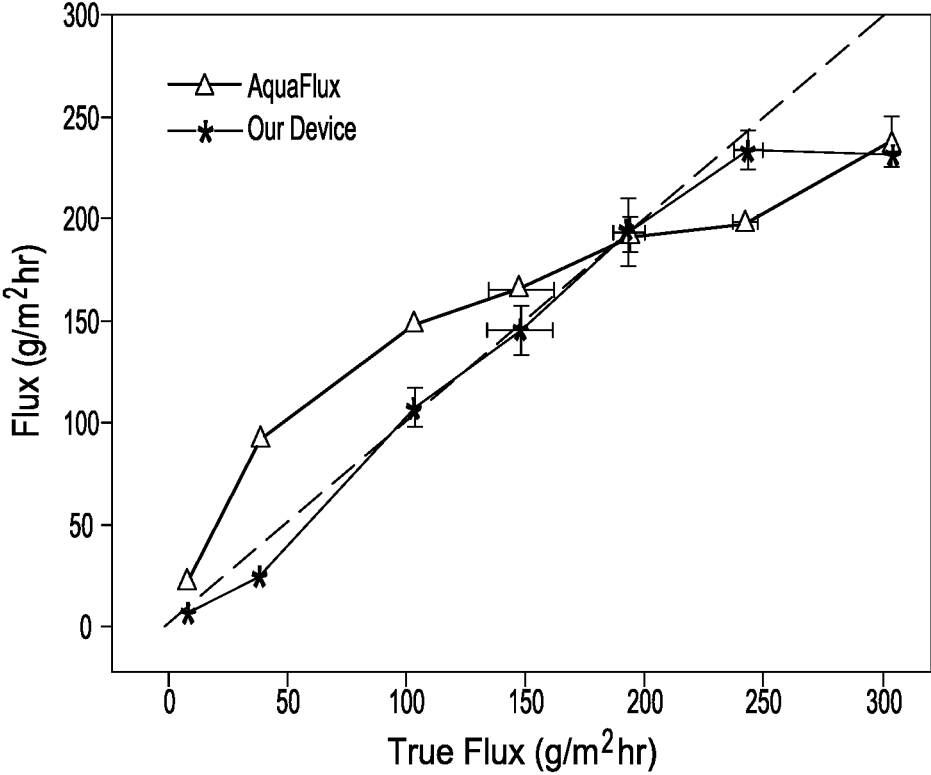
FIG. 10 is a graph showing a comparison of flux measurements from three different devices.

FIG. 10 plots the flux measured by the TEWL device 10 against the true flux measured by the wet-cup method after the correction factor in FIG. 9 is applied and shows good agreement. For comparison, parallel measurements were also performed using an AquaFlux device (P/N: AF200, Biox Systems, UK) equipped with a reduced orifice cap (P/N: AF005-03, Biox Systems, UK) by holding it manually on top of the mesh/membrane in FIG. 8. As shown in FIG. 10, a noticeable discrepancy emerges between the flux measurements derived from the AquaFlux device and the true flux readings, which might be attributed to either external moisture infiltrating the measurement chamber (particularly noticeable in lower flux readings) or moisture escaping into the ambient surroundings (more pronounced with higher flux readings). This leakage issue is significantly mitigated in the case of our device, as a double-sided adhesive tape was used to completely seal the chamber perimeter, thereby enhancing the reliability of our flux measurements.

Figure 11A:
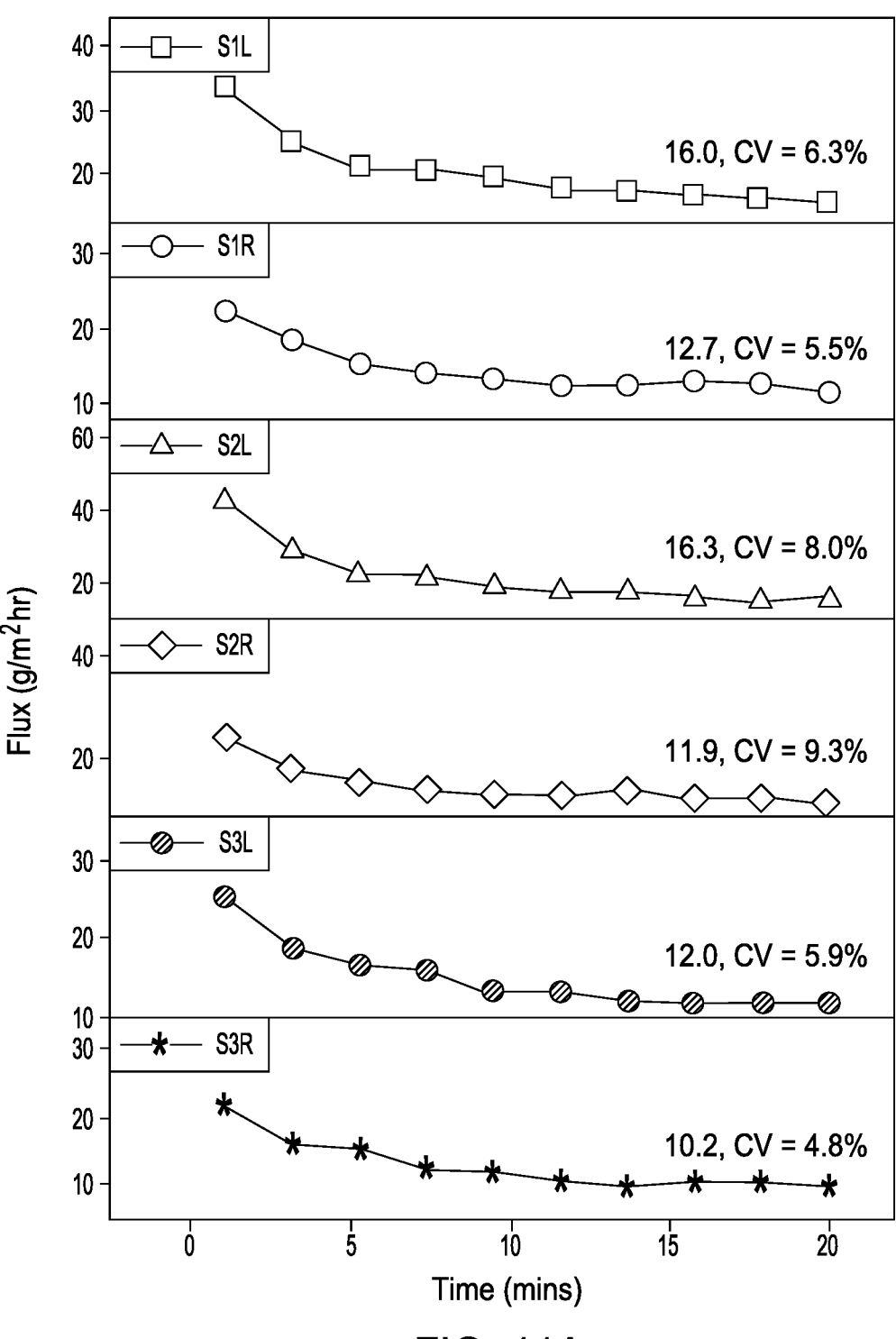
FIGS. 11A-11C are graphs showing water vapor flux measurements at upper arm, forearm and palm of 3 human subjects, respectively.
Figure 11B:
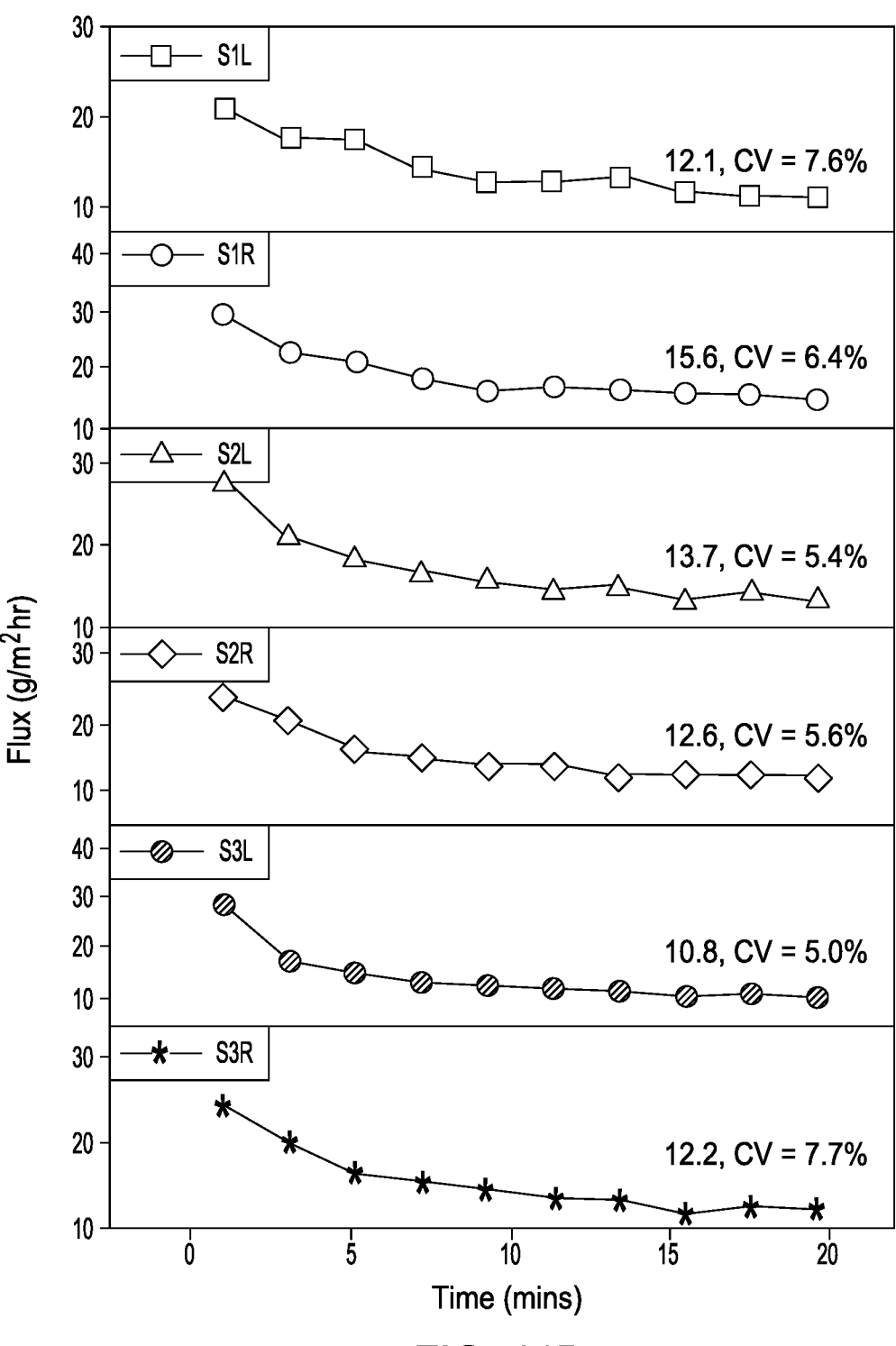
Figure 11C:
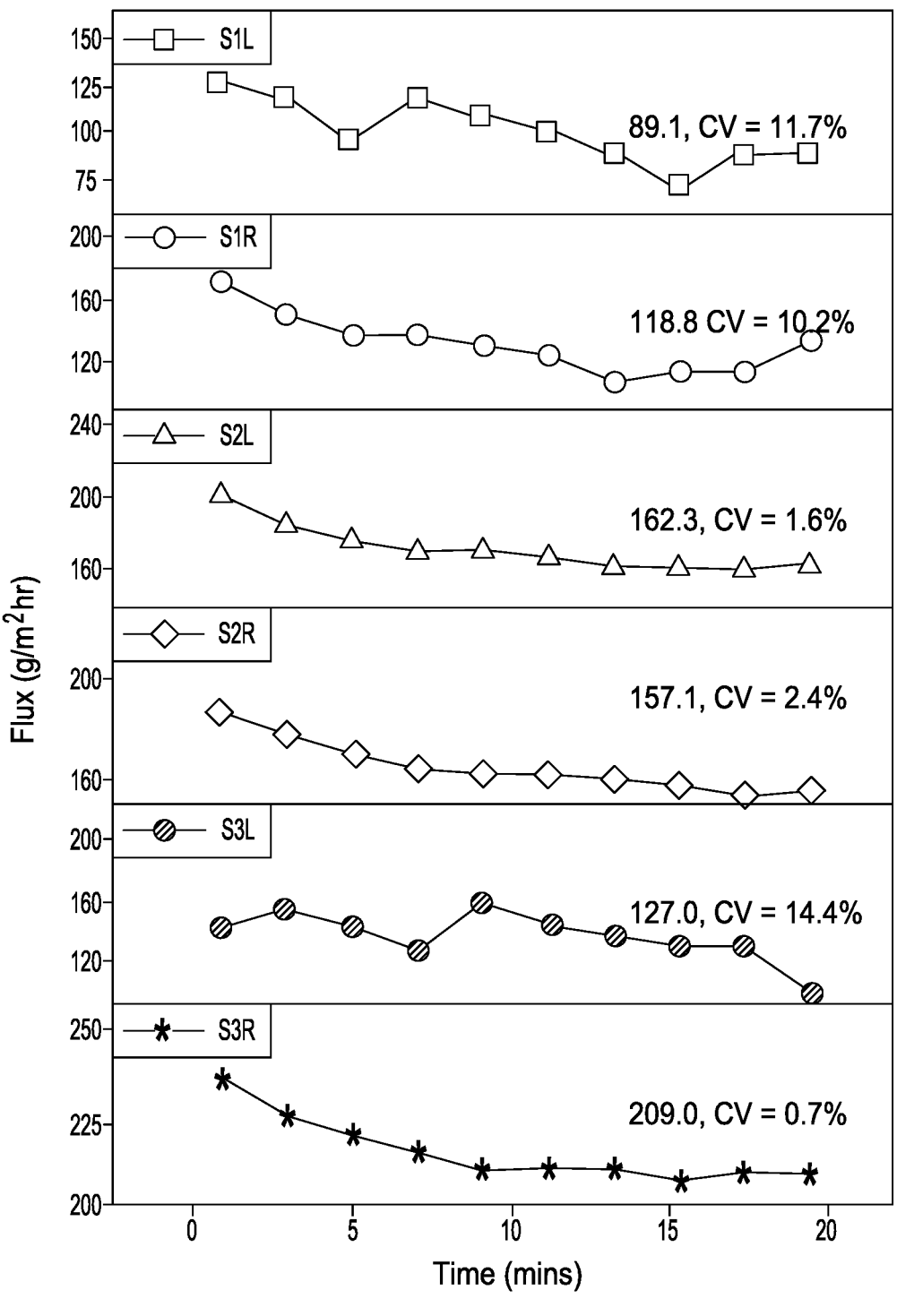

Further testing was done to distinguish between insensible sweating and sensible sweating due to activated sweat gland secretion. With reference to FIGS. 11A-11C, water flux is measured on six different body locations of three human subjects (lab members): left/right upper arm (FIG. 11A), left/right forearm (FIG. 11B), and left/right palm (FIG. 11C). The subjects were asked to sit in a resting position in a room of ~23° C. After the TEWL device 10 was placed on a body location and sealed with a double-sided adhesive film, a waiting time of 20 minutes was given to allow thermal equilibrium to be established between the skin and the TEWL chamber (and the thermocouple). The thermocouple reading increased from room temperature to 28-32° C., since the heat from the skin warms up the TEWL chamber and the skin. The final temperature varies slightly depending on subjects and body locations, indicative of different heat generation rates. Note that here we used the initial 20 minutes of waiting time to examine how the chamber interior environment (and the skin local environment) changes when the TEWL device is mounted onto the skin. In practice, the waiting time can be eliminated and the flux measurement can start immediately after the TEWEL device is mounted.

After the initial waiting time, the flux measurement started. Each flux measurement cycle took 2 minutes, including 60 seconds of dry air flush at a rate of ~90 mL/min through internal air circulation and 60 seconds of RH-T sensor reading. Ten cycles were repeated without interruption. As seen in FIGS. 11A-11C, all the data shows that the vapor flux from the skin decreases progressively during the first 5 or 6 measurements and then gradually levels off, which suggests that the water in the skin (stratum corneum layer) was gradually depleted. It is known that the water vapor flux coming out of the skin has contributions from both insensible sweating (i.e., TEWL) and sensible sweating (or thermal sweating) due to activated sweat gland secretion. Therefore, the initial water vapor flux values measured in FIGS. 11A-11C contain the contributions from both sensible and insensible sweating. Sensible sweating is inevitable when the ambient temperature surrounding the skin region under test is 28-32° C. inside the chamber. The last few flux values, when the water content in the stratum corneum layer has been significantly depleted, result mainly from the sensible sweating, which serves as the background. Further notice that the background flux for the palm is much higher than for upper arm and forearm, since the density of sweat glands in the palm (~520 $glands/cm^2$) is higher than the upper arm (~90 $glands/cm^2$) and forearm (~100 $glands/cm^2$). Finally, the TEWL device exhibits good repeatability as seen in the last 5 flux measurements that have a CV of <10% in most cases, which is due to the closed chamber design and identical initial dry conditions inside the chamber and on the skin surface for each measurement.

The actual TEWL due to insensible sweating can be calculated by subtracting the background from the initial water flux reading (i.e., the flux value at t=2 min–the averaged value of the last 5 readings). For a comparison, parallel experiments were conducted using the AquaFlux device equipped with the reduced orifice cap on the same subjects and same body locations ~3 minutes after the WASP measurement. At this time, skin ambient temperature for AquaFlux measurements was ~23° C. (room temperature), which is within the AquaFlux' specified operation temperature range of 18° C.-28° C., and thus sensible sweating was significantly reduced. In general, for upper arm and forearm measurements, the TEWL obtained by the TEWL device 10 and AquaFlux match well.

By harnessing the adaptable feature of flexible-timed dry air flushes within the TEWL device 10, it also becomes possible to investigate the dynamics of stratum corneum (skin) rehydration. The incorporation of this functionality within the TEWL device holds significant promise for enhancing therapeutic studies involving various topical skin creams and wound healing.

Figure 12A:
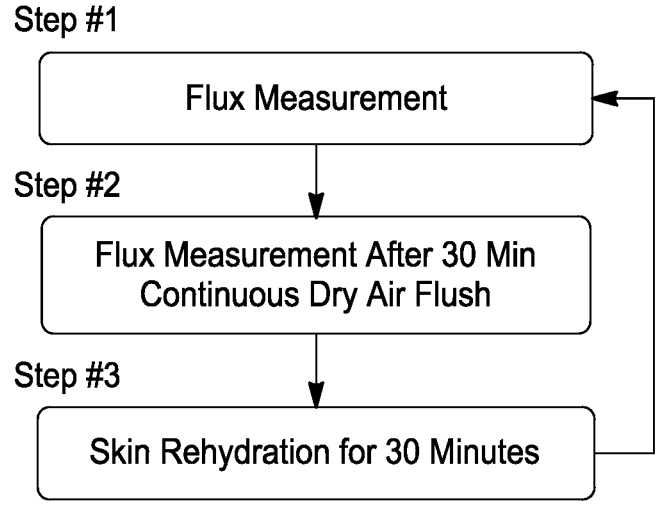
FIG. 12A depicts a process for evaluating skin rehydration.
Figure 12B:
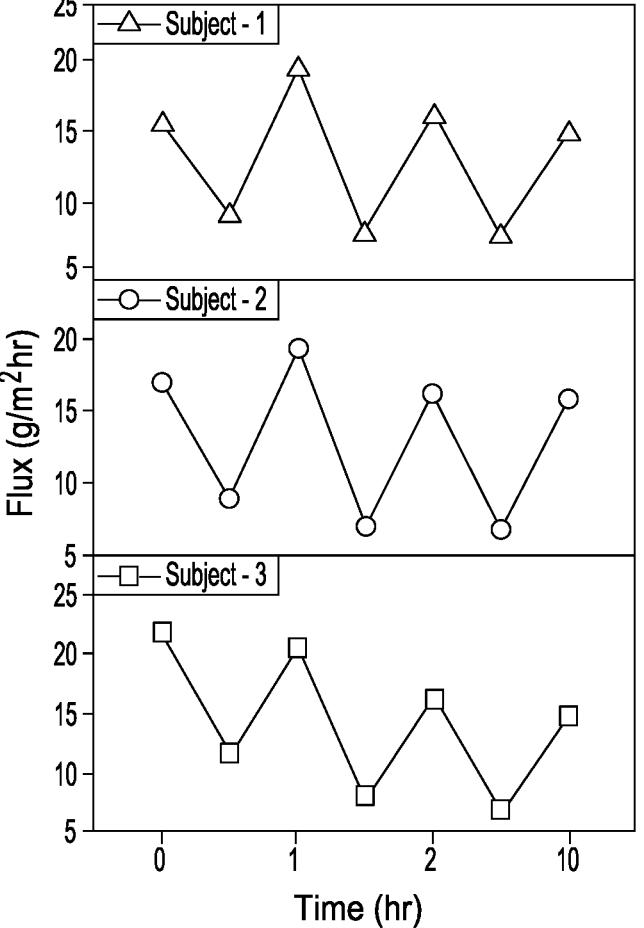
FIG. 12B are graphs showing skin dehydration-rehydration cycles for three different subjects.

To exemplify this functionality, the upper arm skin is subjected to a controlled dehydration interval of 30 minutes, followed by a subsequent rehydration period of 30 minutes. The water vapor flux values were also measured before and after dehydration. This process is illustrated in FIG. 12A. FIG. 12B shows the water vapor flux values on the left upper arm of three human subjects (lab members) during dehydration-rehydration cycles. It can be seen clearly that the water vapor flux decreases after each 30-min of dry air purge (dehydration), suggesting the depletion of the water under the skin (in the stratum corneum layer). The remaining background water vapor flux may be attributed to the sensible sweating, as discussed previously. After 30-min of rehydration, the water vapor flux almost goes back to the original value at t=0 h for two subjects. For Subject-3, water vapor flux is unable to recover fully and shows a slow decreasing trend after each dehydration cycle, suggesting a slower rehydration process than Subjects-1 and 2. The actual TEWL of 8.9 $g/m^2$ hr, 9.4 $g/m^2$ hr, and 9.5 $g/m^2$ hr can be estimated by subtracting the averaged valley flux values from the averaged peak flux values for Subjects 1-3, respectively. For a comparison, the TEWL value of 10.1 $g/m^2$ hr, 10.9 $g/m^2$ hr, and 9.2 $g/m^2$ hr on the same locations for Subjects 1-3 were obtained using AquaFlux before starting the measurements with the TEWL device 10. Again, for AquaFlux measurements, the skin ambient temperature was ~23° C., at which the sensible sweating is suppressed.

In conclusion, the new TEWL measurement method introduced in this disclosure mitigates the issues encountered by its predecessors. Continuous monitoring and wearable feature of this new TEWL method opens up a door for early diagnosis of food allergies and other skin disorders. In addition, with minimal changes in the chamber dimensions, this TEWL method can also be employed to continuously monitor the sweating rate in sports medicine for athletes engaged in strenuous training or endurance competitions.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A transepidermal water loss measurement device, comprising:
    a housing having a measurement chamber enclosed therein, wherein the measurement chamber has an opening configured to be placed against skin of a subject;
    a relative humidity sensor arranged adjacent to or in the measurement chamber and configured to measure relative humidity in the measurement chamber;
    a temperature sensor arranged adjacent to or in the measurement chamber and configured to measure temperature in the measurement chamber;
    an inlet duct residing in the housing and providing a first fluidic channel to the measurement chamber, wherein one end of the first fluidic channel is accessible outside of the housing and other end of the first fluidic channel connects into the measurement chamber;
    an inlet valve disposed in the first fluidic channel;
    an outlet duct residing in the housing and providing a second fluidic channel to the measurement chamber, wherein one end of the second fluidic channel is accessible outside of the housing and other end of the second fluidic channel is connected into the measurement chamber;
    an outlet valve disposed in the second fluidic channel;
    a pump fluidly coupled to the inlet duct and configured to move air through the measurement chamber; and
    a controller operably couples to the pump and is in data communication with the humidity sensor and the temperature sensor, wherein the controller is configured to turn off the pump and close the inlet valve and close the outlet valve during a measurement phase, and the controller is configured to turn on the pump and open the inlet valve and open the outlet valve during a drying phase, thereby allowing the air to move through the measurement chamber.

2. The water loss measurement device of claim 1 further comprises a first filter configured to remove moisture from the air moved by the pump into the measurement chamber.

3. The water loss measurement device of claim 2 further comprises a second filter configured to remove hydrocarbons from the air moved by the pump into the measurement chamber.

4. The water loss measurement device of the 1 wherein the controller is configured to determine water loss through the skin adjacent to the opening of the measurement chamber during the measurement phase.

5. The water loss measurement device of claim 4 wherein the controller is configured to determine water loss through the skin using Fick's first and second law of diffusion.

6. The water loss measurement device of claim 1 is configured to be worn on wrist of the subject.

7. The water loss measurement device of claim 1 further includes means for cooling at least one of the measurement chamber and the skin of the subject.

8. A transepidermal water loss measurement device, comprising:
    a housing having a measurement chamber enclosed therein, wherein the measurement chamber has an opening configured to be placed against skin of a subject;
    a relative humidity sensor arranged adjacent to or in the measurement chamber and configured to measure relative humidity in the measurement chamber;
    a temperature sensor arranged adjacent to or in the measurement chamber and configured to measure temperature in the measurement chamber;
    an inlet duct residing in the housing and providing a first fluidic channel to the measurement chamber, wherein one end of the first fluidic channel is accessible outside of the housing and other end of the first fluidic channel connects into the measurement chamber;
    an outlet duct residing in the housing and providing a second fluidic channel to the measurement chamber, wherein one end of the second fluidic channel is accessible outside of the housing and other end of the second fluidic channel is connected into the measurement chamber;
    a valve disposed in at least one or the first fluidic channel or the second fluidic channel;
    a pump fluidly coupled to the inlet duct and configured to move air through the measurement chamber; and
    a controller operably couples to the pump and is in data communication with the humidity sensor and the temperature sensor, wherein the controller is configured to turn off the pump and close the valve during a measurement phase, and the controller is configured to turn on the pump and open the valve during a drying phase.

9. The water loss measurement device of claim 8 further comprises a first filter configured to remove moisture from the air moved by the pump into the measurement chamber.

10. The water loss measurement device of claim 8 further comprises a second filter configured to remove hydrocarbons from the air moved by the pump into the measurement chamber.

11. The water loss measurement device of the 8 wherein the controller is configured to determine water loss through the skin adjacent to the opening of the measurement chamber during the measurement phase.

12. The water loss measurement device of claim 11 wherein the controller is configured to determine water loss through the skin using Fick's first and second law of diffusion.

13. The water loss measurement device of claim 8 is configured to be worn on wrist of the subject.

14. The water loss measurement device of claim 8 further includes means for cooling at least one of the measurement chamber and the skin of the subject.

* * * * *